(12) United States Patent
Wilkie et al.

(10) Patent No.: US 7,201,169 B2
(45) Date of Patent: Apr. 10, 2007

(54) MASK

(75) Inventors: Paul Wilkie, New South Wales (AU); Colin Sullivan, New South Wales (AU)

(73) Assignee: Australian Centre for Advanced Medical Technology Ltd., New South Wales (AU)

( * ) Notice: Subject to any disclaimer, the term of this patent is extended or adjusted under 35 U.S.C. 154(b) by 535 days.

(21) Appl. No.: 10/311,457

(22) PCT Filed: Jun. 18, 2001

(86) PCT No.: PCT/AU01/00721

§ 371 (c)(1),
(2), (4) Date: Feb. 13, 2003

(87) PCT Pub. No.: WO01/97892

PCT Pub. Date: Dec. 27, 2001

(65) Prior Publication Data

US 2003/0172936 A1     Sep. 18, 2003

(30) Foreign Application Priority Data

Jun. 19, 2000 (AU) .................................. PQ8215

(51) Int. Cl.
*A61M 15/08* (2006.01)
*A62B 18/02* (2006.01)

(52) U.S. Cl. ............................. 128/207.18; 128/207.13

(58) Field of Classification Search ..................... None
See application file for complete search history.

(56) References Cited

U.S. PATENT DOCUMENTS

| | | | |
|---|---|---|---|
| 2,693,800 A | | 11/1954 | Caldwell |
| 2,735,432 A * | | 2/1956 | Hudson .................. 128/207.18 |
| 4,284,076 A | | 8/1981 | Hall et al. |
| 4,367,735 A * | | 1/1983 | Dali ....................... 128/207.18 |
| 4,782,832 A * | | 11/1988 | Trimble et al. ......... 128/207.18 |
| 5,046,491 A | | 9/1991 | Derrick |
| 5,490,504 A | | 2/1996 | Vrona et al. |
| 5,513,635 A | | 5/1996 | Bedi et al. |
| 5,682,881 A | | 11/1997 | Winthrop et al. |
| 5,724,965 A | | 3/1998 | Handke et al. |
| 5,752,511 A | | 5/1998 | Simmons et al. |
| 6,431,172 B1 * | | 8/2002 | Bordewick ............. 128/207.18 |
| 2001/0029954 A1 * | | 10/2001 | Palmer .................. 128/207.17 |

FOREIGN PATENT DOCUMENTS

| WO | WO 99/04842 | 2/1999 |
|---|---|---|
| WO | WO 00/74758 A1 | 12/2000 |

OTHER PUBLICATIONS

U.S. Appl. No. 60/201,935.*
U.S. Appl. No. 60/186,859.*

* cited by examiner

*Primary Examiner*—Glenn K. Dawson
(74) *Attorney, Agent, or Firm*—Browdy and Neimark, PLLC

(57) ABSTRACT

A mask (10) for supplying gas under pressure to the nasal airway of a human includes a manifold (30) including means (36) for connection to a gas supply means, a gas supply element or elements (26) for providing said gas to the nasal airway without pressurising the exterior of the nose and a flexible strap (12) formed from an elastomeric material for securing the manifold (30) in position. The strap (12) extends either side of the manifold (30) and is shaped to generally conform with the shape of the upper lip and adjacent cheek area to act as a distributed anchor means for the mask (10).

13 Claims, 20 Drawing Sheets

MASK

FIELD OF THE INVENTION

This invention relates to a mask for supplying gases, typically fresh air or oxygen to the airways of humans.

BACKGROUND OF THE INVENTION

Various different types of masks are used to provide fresh air or oxygen to the airways of humans. A specialised category of masks is used to provide positive pressure to the human airway. Positive pressure applied in this manner has two different goals.

In a first category, positive pressure is applied to the lungs for the purpose of stabilising the lungs, and in particular for maintaining a minimum inflation level of the small air spaces in which gas transfer occurs (the alveoli). This therapy is very useful in patients with a variety of lung diseases, where the disease process tends to lead to collapse (closure of the airway containing regions of the lung).

In a second category, the positive pressure is applied to the nasal airway with the intention of maintaining the pressure in, and the patency of, the upper airway. This form of positive airway pressure is known as nasal continuous positive airway pressure (nasal CPAP). This is now the "gold standard" treatment for the condition known as obstructive sleep apnea (OSA), and also for snoring. Obstructive sleep apnea is a condition in which the upper airway closes in sleep, and does so repeatedly. Nasal CPAP, when applied for the duration of sleep, stabilises the upper airway and allows for normal sleep and normal breathing.

Masks for applying nasal CPAP, or nasal pressure support ventilation have a requirement to be able to deliver pressure and flow and maintain pressures within the mask without permitting leaks. Leaks are undesirable as they can allow the pressure in the mask to drop below a therapeutic level. Leaks may also be an irritation particularly, if the leak causes jets of air/oxygen to be directed into the patient's eye. Leaks interrupt a patient's sleep which is undesirable as interrupted sleep is known to be of much less value than uninterrupted sleep. Leaks may also be noisy. Further, as the masks are for use during natural sleep, a high level of comfort in the fit of the mask is necessary.

Numerous different types and structures of mask have been proposed to address or alleviate the problems described above, most of which are directed to achieving a good comfortable seal.

In the past few years, in order to achieve a good seal, "bubble" type gas delivery masks have been developed. One such mask is described in Australian Patent No. 643994, dated May 16, 1991. The mask described therein has a face contacting portion which is formed from an elastomeric material and is shaped to define a large bubble or dome shaped chamber. When gas is delivered through the chamber, the chamber tends to balloon outwardly and, when fitted to a patient, the face contacting portion is caused to overlay a region of the patient's face and seal three dimensionally with the contours of the overlaid facial region. For practical reasons the mask is integrated with a rigid shell-like moulding which does not contact the patient's face. The shell is provided to enable a gas supply line to be connected to the mask to facilitate fastening of the mask to a patient's face and to minimise the risk that movement of the gas supply line will disrupt the seal between the mask and the patient's face.

When designing a mask, the mask must be able to achieve an air tight seal with the subject's face and at the same time be sufficiently comfortable to be able to be worn for hours without causing discomfort to the subject and in particular to allow the subject to sleep.

Movement of the head, and subsequent dislodgment of the mask, and breakage of the seal are major problems with prior art masks. This is a particular problem when a patient lies on their side, with the side of their head on the pillow as the rigid manifold tends to contact the pillow. The contact moves the manifold relative to the patient's face, is transmitted to, and affects the integrity of the seal. The manifold can also be pushed onto the patient's nose causing discomfort to the patient.

A further problem for all masks is that an air delivery pipe must be attached to the mask at some point. Movement of the head and the pipe leads to torsion which is transmitted through the hard shell of the manifold and can cause the sealing margins of the mask to rise up and allow a leak. The above-referenced "bubble mask" patent. (Australian patent No 634994), tries to address this by having a "universal joint" between the air delivery pipe and the rigid manifold. Australian Patent No 684412 which is a development of AU 634994, by the same inventor as the earlier Australian patent No 634994, addresses this problem by making a portion of the wall containing the gas supply port exhibit a degree of flexibility that is greater than that of adjacent regions of the mask so that movement by the connecting gas supply line will be accommodated at least in part by flexing of the wall portion. Whilst both masks produce relatively satisfactory seals they are quite bulky, relatively heavy and ungainly. They have a substantial impact or "footprint" on the patient's face. Neither fully solves the problems of forces acting on the manifold causing leaks.

In existing facial masks, because the straps must anchor onto a rigid point, they are attached to the rigid manifold; the result is that typically the strap leaves the side of the face near the cheeks, and passes through air until it reaches the lug on the manifold. This "floating" part of the strap, provides a significant weakness and adversely affects the integrity of the seal when the patient's head moves. When the subject rolls onto their side, this floating part of the strap is easily distorted, and pulls on the mask and leads to a leak.

All masks have to take account of the geometry of the patient's face, in particular the geometry of the patient's nose. Most existing masks are quite bulky and can be quite obtrusive, particularly for patients who either wear glasses or wish to read while falling asleep or who have facial hair.

Beards also adversely affect the sealing of conventional masks. Often patients who suffer from sleep apnea are obliged to shave their beards if thee wish to receive treatment via a nasal mask.

One mask which does not require a patient to shave, and allows the wearing of glasses is the Respironics® Simplicity™ nasal mask, manufactured by Respironics Inc., of 1501 Ardmore Boulevard, Pittsburg, Pa. That mask provides a bubble type seal which fits over a patients nose only extending up to the bridge of the nose and around the sides. While this reduces the "footprint" of the mask on the patient's face, the reduction in the size of the sealing bubble compared with the traditional bubble masks described above reduces the area of sealing and makes the mask much more susceptible to torsional effects caused by movement of the patient's head, pulling on the gas supply pipe etc. The seal is much less "stable" than traditional bubble masks.

U.S. Pat. No. 4,782,832 adopts a different approach to the above described masks in providing what it terms a "nasal puff". The gas delivery mask/nasal puff of U.S. Pat. No. 4,782,832 fits only in the nose of the patient and is thus of a relatively small size. The nasal puff includes a plenum chamber from which project a pair of generally conical soft synthetic gas delivery elements for insertion into a patient's nares. Each element includes a bellows type corrugated section which allow the gas delivery elements to flex and pivot relative to each other and to the plenum to fit a variety of patients. This bellows is to allow for the prong to adjust for minor differences in angle. The nasal mask is fitted to a patient by means of a harness.

One major problem with the nasal puff shown in U.S. Pat. No. 4,782,832 is that because the gas delivery elements effectively anchor the mask in place, any torsion on the mask due to twisting or movement of the patient's head, or pulling or twisting of the air delivery pipe connected to the mask is transmitted to the delivery elements and thence to the patient's nares. The layer of skin (the nasal epithelium) inside a patient's nose is highly sensitive to contact, and particularly to rubbing contact. Consequently, the anchoring of the nasal puff of U.S. Pat. No. 4,782,832 by means of the gas delivery elements extending into the nares is a fundamental flaw in the design.

The present invention seeks to provide an improved mask which reduces the relative size, weight and bulk of the existing masks and yet provides a satisfactory seal and may be held to the face with greater stability.

SUMMARY OF THE INVENTION

In a first broad aspect, the present invention provides a mask means for supplying gas under pressure to the nasal airway of a human comprising:

a manifold including means for connection to a gas supply means;

a gas delivery element or elements for providing gas under pressure to the nasal air way of a human without pressurising the sides of the nose;

a flexible strap formed from an elastomeric material for securing the manifold in position on the face of a human, the strap defining a first side and a second opposite side and extending either side of the manifold, the first side of the strap being shaped and configured to generally conform with the shape of the upper lip and adjacent cheek area of a human to act as a distributed anchor means for anchoring the nasal mask when the mask is located on said human face, in use, wherein the manifold is disposed to the second side of the strap such that, in use, the manifold is anchored by the strap but not compressed between the strap and the human's face.

In one embodiment the gas delivery elements comprise nasal prongs which locate inside a patient's nostrils.

Thus, according to one preferred aspect of the present invention, there is provided a mask for supplying gas under pressure to the nasal airway of a human comprising:

a manifold including means for connection to a gas supply means and defining a flexible shaped bubble made from an elastomeric material having an aperture therein which is adapted to seal 3-dimensionally to the base of a human's nose supplying air to the human's naris without pressurising the exterior of the patient's nose; and a flexible strap formed from a flexible elastomeric material for securing the manifold to the face of a human, the strap defining a first side and a second opposite side and extending either side of the manifold, the first side of the strap being shaped and configured to generally conform to the shape of the upper lip and adjacent cheek area to act as a distributed anchor means for anchoring the nasal mask to a human's face when the mask is located on said human face, in use, wherein the manifold is disposed to the second side of the strap such that in use the manifold is anchored by the strap but not compressed between the strap and the human's face.

The advantage of the present invention, in contrast with the prior art U.S. Pat. No. 4,782,832, is that the gas delivery elements do not function as the primary anchor means but merely act as a delivery/sealing means for the air pressure. Instead, anchoring is provided by the strap which provides an elongate anchor means with a large contact area to the face which is therefore very secure, movement being prevented by a high degree of contact by the strap and the skin with consequently high frictional force. The separation of the sealing functions and the anchoring functions is also a major step forward over the bubble type masks of AU 643994 et al where the bubble membrane acts not only as the seal around a patient's nose but also has to anchor the mask to the patient's face. By separating the sealing and anchoring functions the seal is less likely to be broken or adversely affected by movement of the patient's head. The strap is made from a flexible elastomeric material such as silastic and typically the manifold will be formed from the same flexible material so that the manifold itself, is also deformable. The gas delivery elements may also be formed from silastic.

The strap may form one side of the manifold.

Although the nasal mask could theoretically function with two anchor points, a third anchor point is preferable. In one preferred embodiment, this is provided by a nose bridging portion which extends from the manifold and is shaped to span the patient's nose in use. A distal end of the bridging portion defines a pad which may include a slot for attachment to a harness and an inlet adapted for coupling the nasal mask with a source of gas. The extension of the manifold is preferably configured, so that in use, when the mask is secured to a patient's face, the extension passes over the patient's nose.

This arrangement is particularly advantageous as the shape of the patient's nose no longer needs to be taken into account in designing masks.

The nose-bridging portion improves the anchoring of the mask yet keeps the footprint of the mask on patient's face at a minimum.

The mask may include a bubble membrane in place of the nasal prongs.

Thus in a second preferred aspect of the present invention there is provided a mask for supplying gas under pressure to the nasal airway of a human comprising:

a manifold including means for connection to a gas supply means and defining a flexible shaped bubble made from an elastomeric material having an aperture therein which is adapted to seal three-dimensionally to the base of a human's nose supplying air to the human's naris without pressurising the (sides) exterior of the patient's nose; and a flexible strap formed from a flexible elastomeric material for securing the manifold to the face of a human, the strap extending either side of the manifold and being shaped and configured to generally conform to the shape of the upper lip and adjacent cheek area to act as a distributed anchor means for anchoring the nasal mask to a human's face.

This embodiment of the mask in which the interior, but not the exterior of the nose/nostrils is subject to raised pressure, causes the nostrils to expand and thus reduces the resistance to air flow.

Although the nasal mask could theoretically function with the strap extending either side of the manifold acting as two anchor points, a third anchor point is preferable. In one embodiment, this may be provided by a nose bridging portion in the form of a pipe or duct which extends from the manifold and is shaped to pass over the patient's nose in use. A distal end of the bridging portion defines a pad which may include a slot for attachment to a harness and an inlet adapted for coupling the nasal mask with a source of gas. However, it is preferred that two pipes extend either side of the patient s nose and join at a distal end which again defines a pad which may include a slot for attachment to a harness and an inlet adapted for coupling the nasal mask with a source of gas. The two pipes are most preferably shaped to closely fit to the contours of the patient's face and each pipe passes between one of the patient's eyes and the contiguous side of the patient's nose. In this way the pipes function as a barrier between the seal around the patient's nose and the patient's eyes and deflect any gas or air leaks escaping from the seal away from the patient's eyes which are sensitive to air leaks. This mask also has the advantage of having a very low profile compared to existing masks.

In a yet further embodiment a further pipe way extend along one side of the strap typically with one wall of the pipe being defined by the strap. One pipe could be used to supply air to the mask and the other for airflow out of the mask, the outflow pipe at least would typically include a one way valve. Meters could be placed in the two pipes to measure in and out gas flow, or gas concentrations or the like. Such a mask could be useful for treating and/or monitoring stroke victims and the like who may require a supply of pressurised air or oxygen, the low profile of the mask being a particular advantage.

The type of bubble described above in which the interior, but not the exterior of the nose/nostrils is subject to raised pressure may also be used in masks where the strap does not define a distributed anchor means.

Thus in a yet further aspect of the present invention there is provided a mask for supplying a gas under pressure to the nasal airway of a human's nose, the nose having a side, and a base defining nares comprising:

a manifold including means for connection to a gas supply means;

a flexible shaped bubble membrane made from a elastomeric material, the bubble membrane defining an aperture of about the size of the base of a human nose;

means for locating and securing the aperture of the bubble membrane at the base of the human's nose;

means for supplying air under pressure from the manifold to the bubble membrane wherein in use, when gas is supplied under pressure to the bubble membrane with the aperture located at the base of the nose, gas under pressure flows into the nares expanding the anterior nasal cavities thereby reducing the resistance to air flow, and simultaneously causing a skin contact region of the base of the nose to mould and conform to the expanding bubble membrane, thus providing an effective seal.

BRIEF DESCRIPTION OF THE DRAWINGS

Specific embodiments of the invention will now be described, by way of example only, and with reference to the accompanying drawings in which.

DETAILED DESCRIPTION OF PREFERRED EMBODIMENTS

Figure 1:
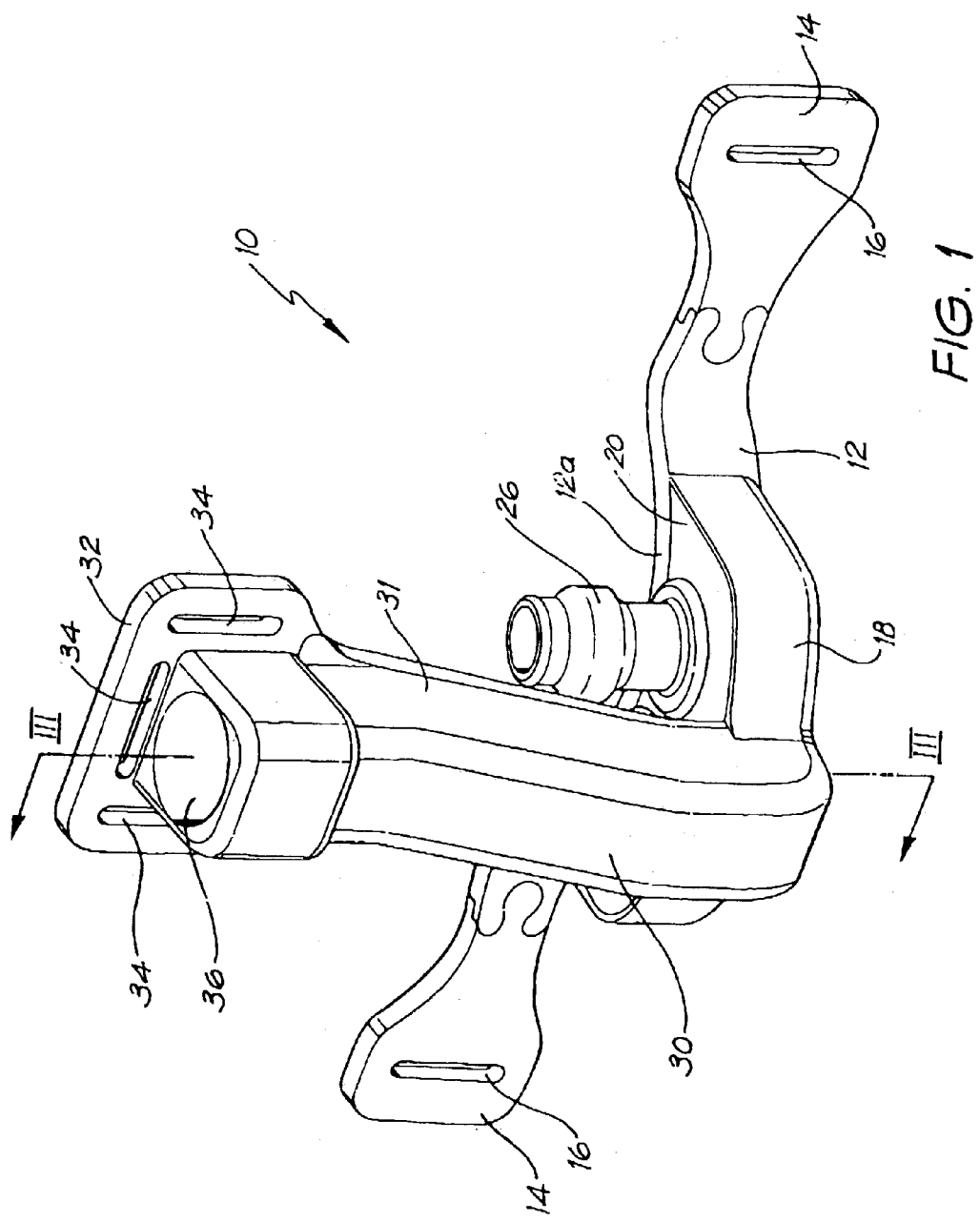
FIG. 1 is an isometric view of a first embodiment of a mask of the present invention.
Figure 2:
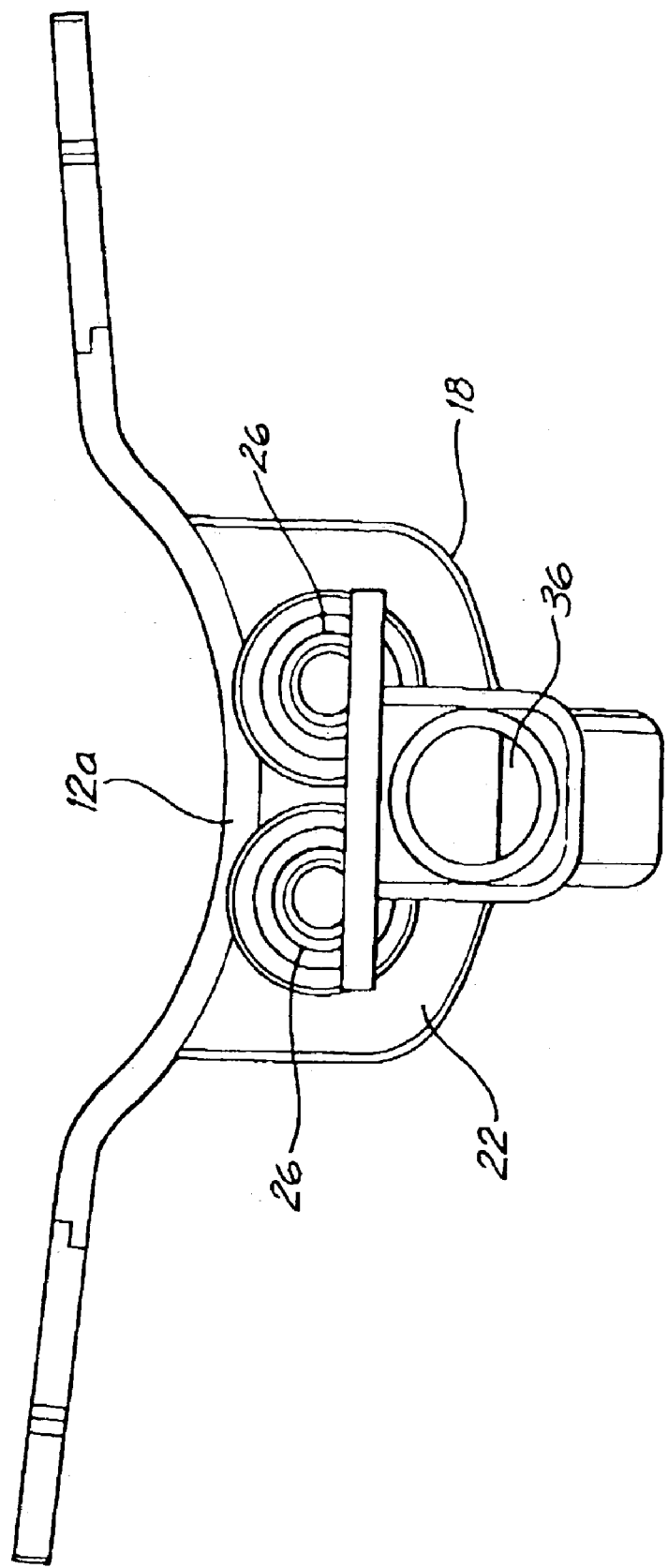
FIG. 2 is an top plan view of the mask shown in FIG. 1.
Figure 3:
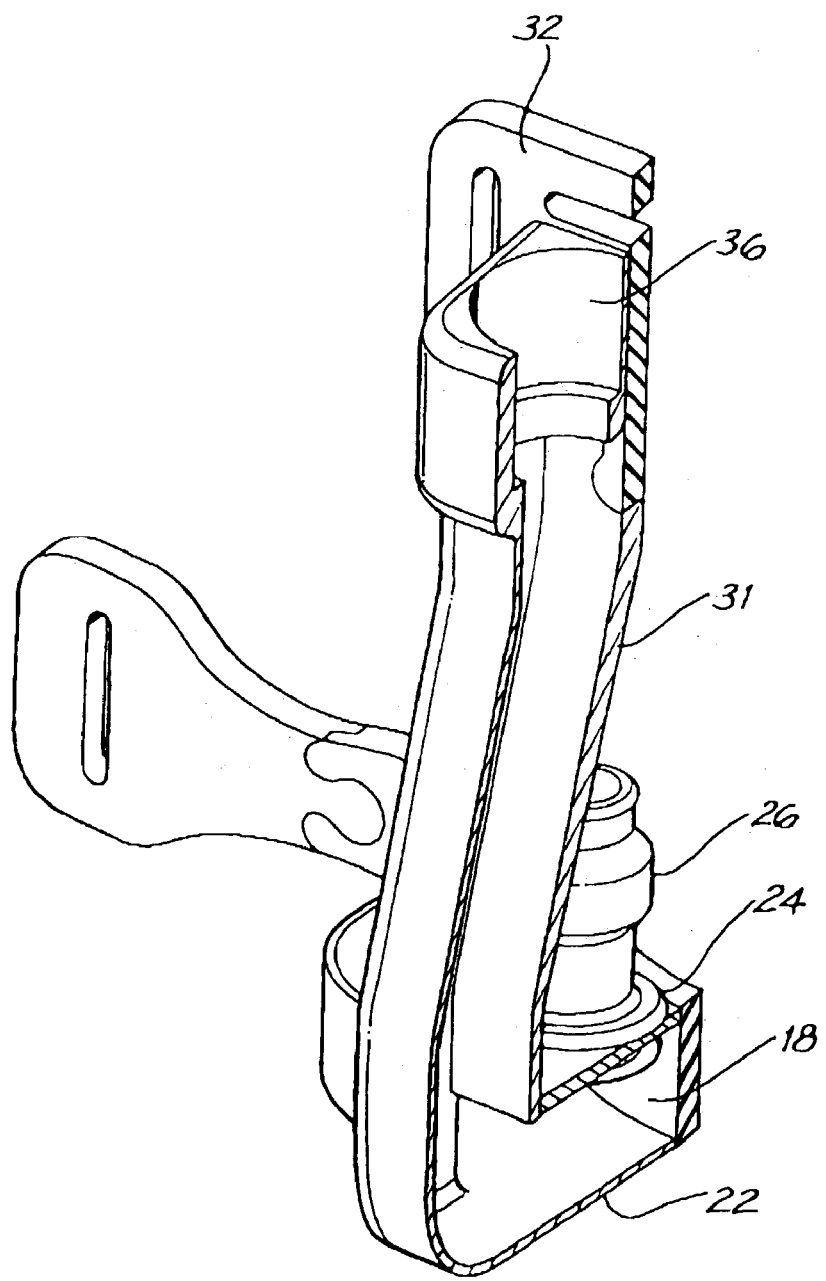
FIG. 3 is a sectional view through the mask shown along lines III—III of FIG. 1.

Referring to the drawings, FIGS. 1 to 3 show a first nasal mask 10. The mask includes a lower strap 12 at each end of which are disposed pads 14, which are enlarged relative to the width of the strap. Each pad 14 defines a slot 16 for the attachment of a harness, not shown in FIGS. 1 to 3 to the mask. The strap is made from a flexible elastomeric material such as silastic and is shaped so that the central area 12a of the strap is curved to generally conform to the shape of the area of a human face between a human's mouth and the base of their nose (see FIG. 2). Note that hereinafter the human is referred to as a patient. On the opposite side of the central area of the strap 12a which contacts a patient's face, there is a manifold or chamber 18. The manifold is also made from the same flexible elastomeric material as the strap. The manifold has a generally planar upper surface 20 and a generally planer lower surface 22. Two circular outlets 24 are provided in the generally planar upper surface to which are attached two gas delivery elements or nasal prongs 26 which, in use, when the mask is correctly positioned on a patient's face, locate and seal inside each naris of the patient's nose. The design of the nasal prongs 26 is shown in more detail in FIG. 4 and discussed in detail below.

Figure 6:
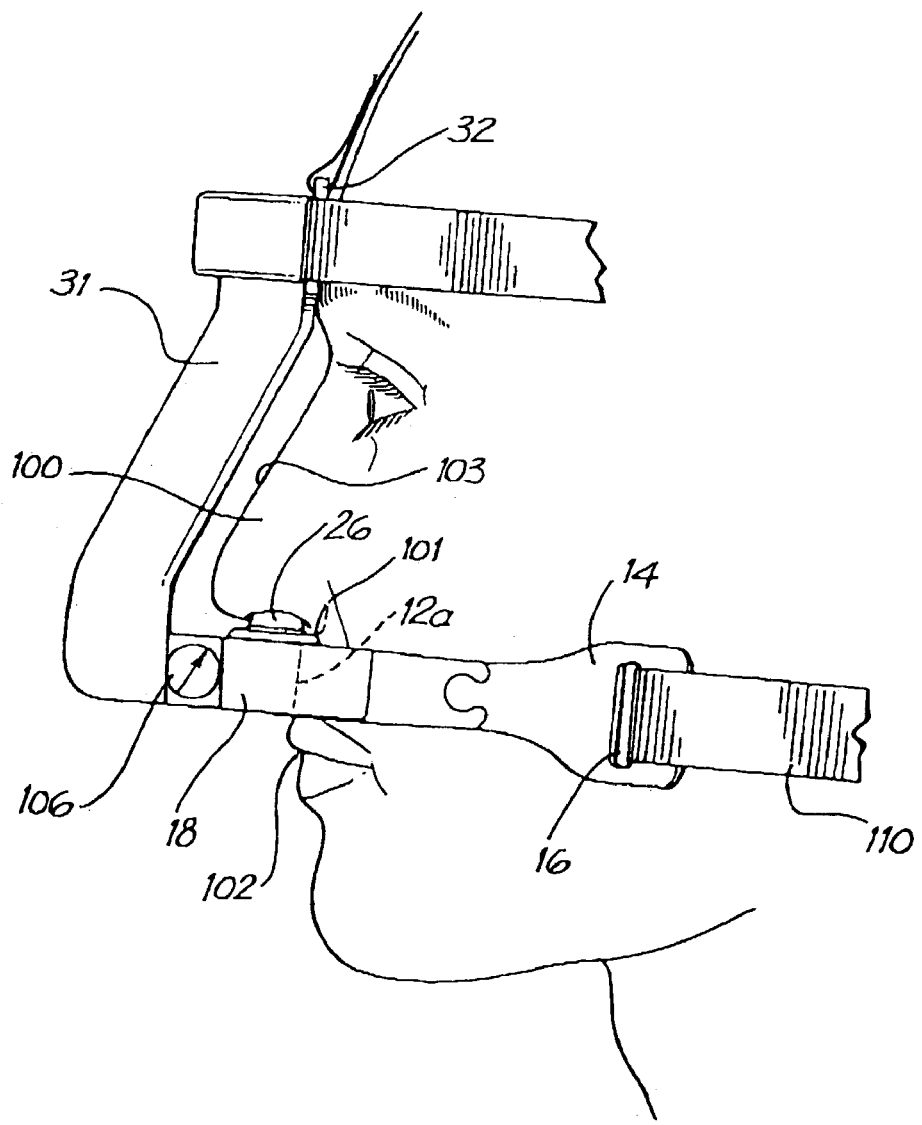
FIG. 6 is a schematic side view illustrating the use of the mask of FIG. 1 on a patient.
Figure 7:
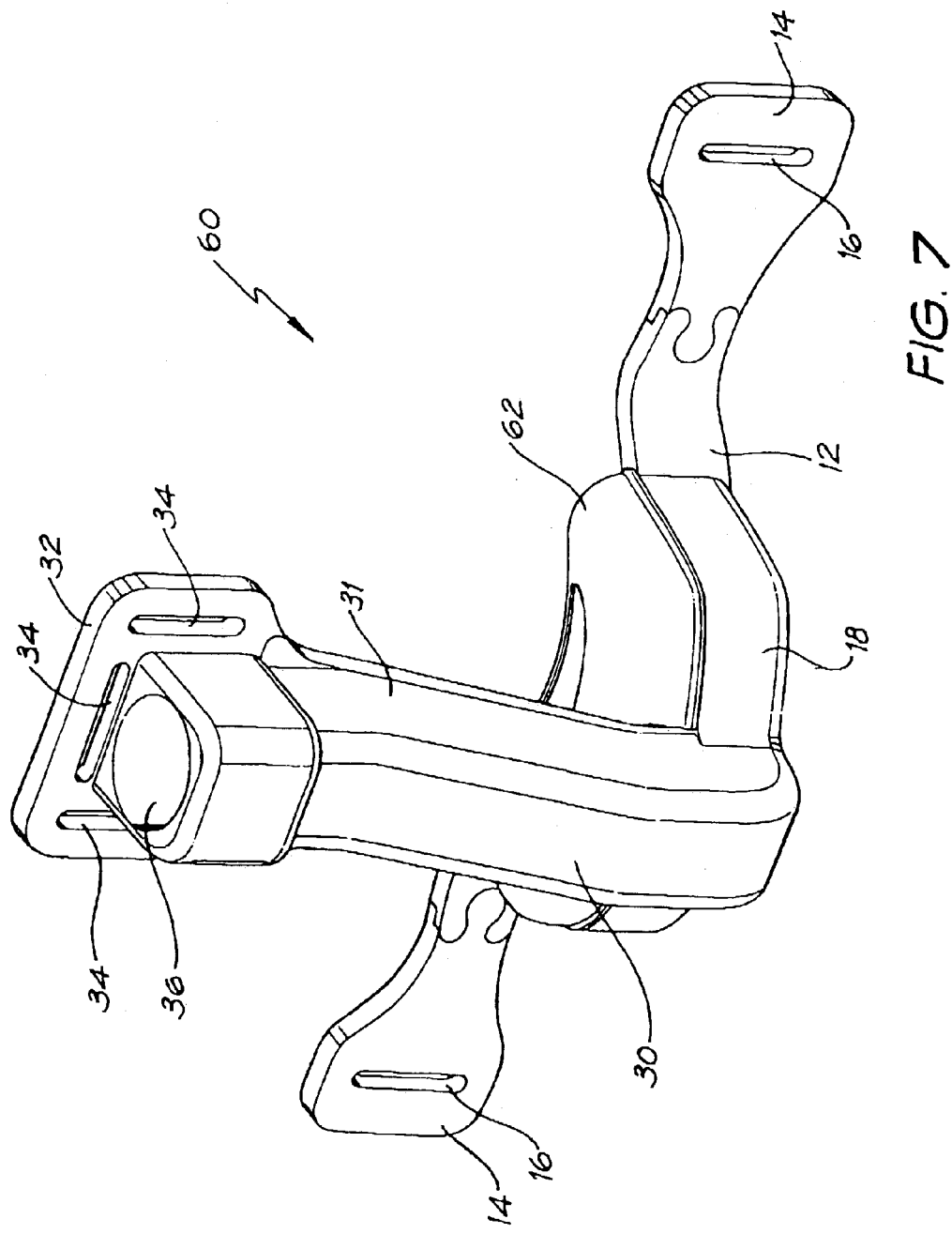
FIG. 7 is an isometric view of a second embodiment of a mask of the present invention.

An inlet pipe 30 extends into the front of the manifold. The inlet pipe defines a bridge portion 31 which extends from the manifold to an anchor pad 32 at the distal end of the pipe remote from the manifold. The bridge portion 31 is aligned generally with a patient's nose. In use, when the mask is fitted to a patient (see FIG. 6), the bridge portion 31 extends above and generally parallel to the upper surface of a typical patient's nose to a point on the patient's forehead just above their nose. The pad 32 includes three slots 34 for receiving a harness 110 in use such as that shown in FIG. 16 which harness is shown in use with a different mask embodiment. The distal end of the pipe 30 also defines a port 36 for receiving an air delivery pipe.

Figure 4:
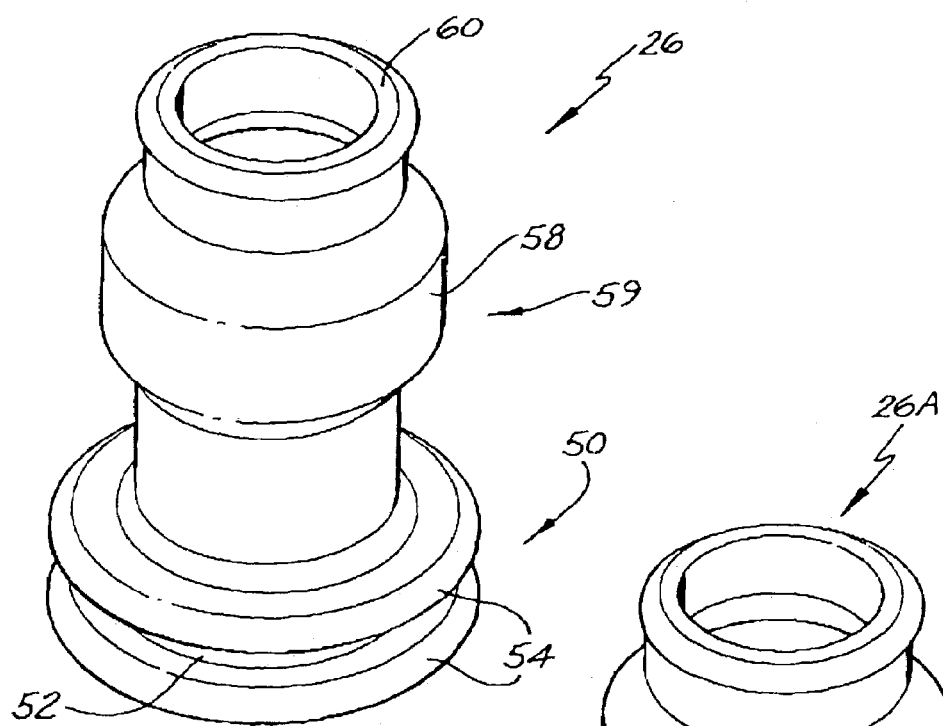
FIG. 4 shows an enlarged isometric view of a nasal prong of the present invention.

FIG. 4 shows the nasal prong 26 in more detail. The prong is generally rotationally symmetrical about its central axis. The base 50 of the prong defines a recess 52, between two ribs or corrugations 54. This recess engages inside the outlet 24 of the upper surface of the manifold with one corrugation above and one below the upper surface 20 to secure the prong to the manifold. The prong is generally cylindrical having an annular cross section but defines an expanded cylindrical section 58 close to the open top 60 of the prong. The upper part 59 of the prong is, like the rest of the mask made of silastic. The wall thickness of the upper part of the prong is 1.5 to 2 mm, except for the expanded section 58 which has a thickness of about 0.2 mm–0.4 mm.

In use, the mask is anchored to a patient's face by means of a harness (such as harness 110, illustrated in FIG. 16) with the engagement area 12a of the strap providing a distributed anchoring means acting between the base 101 of patient's nose 100 and the patient's mouth 102 which through the contact of the central area of the strap 12a directly with the patient's face and also the contact of the sides of the strap 12 directly against the patient's cheeks, retains the manifold in its correct position on the patient's face by frictional forces.

The bridge portion 31 and anchor pad 36 which is also connected to the harness provide a "third" anchor point. This is illustrated schematically in FIG. 6. As can be seen, the bridge portion 31 is spaced from and extends generally parallel to the ridge 103 of the patient's nose.

When the prongs are located inside a patient's naris and pressurised air is fed into the mask and out through the outlets into the prongs the prongs expand upwards into the naris due to the increased pressure inside the prong and the relatively thin walled expanded portion 58 expands and balloons outwards and seals inside the naris. The expansion of the prongs may expand the patient's nostrils, thus reducing resistance to air flow and enabling lower air pressure to be used, if desired. It is important to note that while the pressure inside the patient's nostrils and nasal airway increases, the pressure outside does not. Hence, the patient's nostrils may expand due to the differential pressure between the interior and exterior of the nose. The improved sealing also allows larger pressures (up to 20 cm of water) to be used without leakage, if desired.

Figure 5:
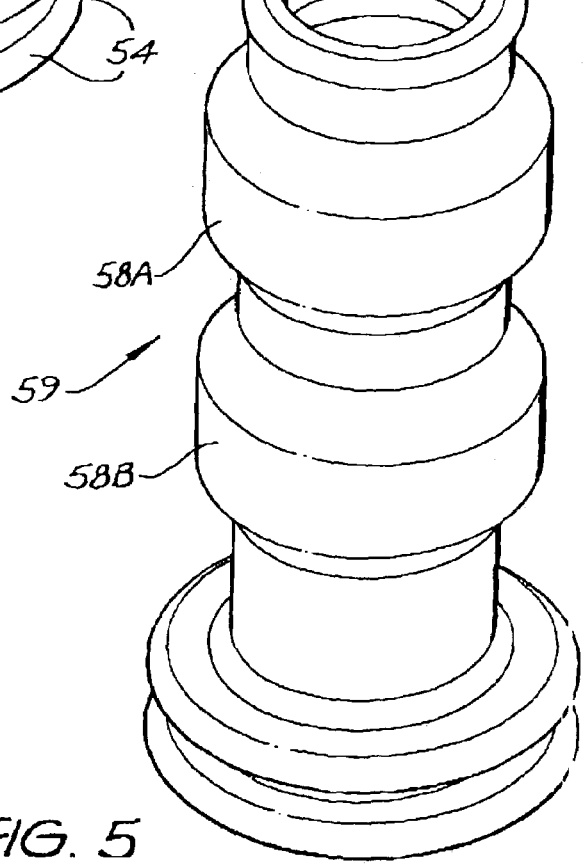
FIG. 5 shows a variant of the nasal prong of FIG. 4.

FIG. 5 shows a variant 26A on the nasal prong which includes two spaced apart expanded/balloon portions 58A, 58B, on the upper part 59 of the prong, one portion 58A expands inside the naris, the other portion 58B expands outside the nose and partly in the opening of the nostril, thus providing a double seal.

The anchoring of the mask and manifold by the strap portion 12a means that the nasal prongs only have to seal and deliver air to the patient's nose and do not have to anchor the mask in position. This contrasts with existing masks where sealing and anchoring are performed by the same elements. One advantage of this is that the nasal prongs do not cause any substantial irritation to the patient's nasal epithelium.

The structure of the bridge portion and in particular, the way it passes over the top of a patient's nose, means the mask is less obtrusive than existing masks and is consequently relatively comfortable.

In a preferred embodiment, a flow meter 106 may be provided in the manifold.

FIGS. 7 to 11 illustrate a second embodiment of the present invention which has the advantage of providing reduced resistance to air flow, in use. The maximum resistance to air flow through a nose occurs at the start of the nasal passage adjacent the nostril or naris. The use of nasal prongs of the type shown in U.S. Pat. No. 4,782,832 reduces the dimensions of the passage and thus can increase resistance further. The embodiment of FIGS. 7 to 11 addresses this problem by providing a flexible bubble membrane which expands and seals around the base of a patient's nose but which does not penetrate the naris. This second embodiment retains the advantage of the separation of the sealing and anchoring functions.

The second embodiment 60 shares a large number of components with the first embodiment which share the same reference numerals in the drawings and the detailed description of those common components is not repeated in detail here.

Figure 8:
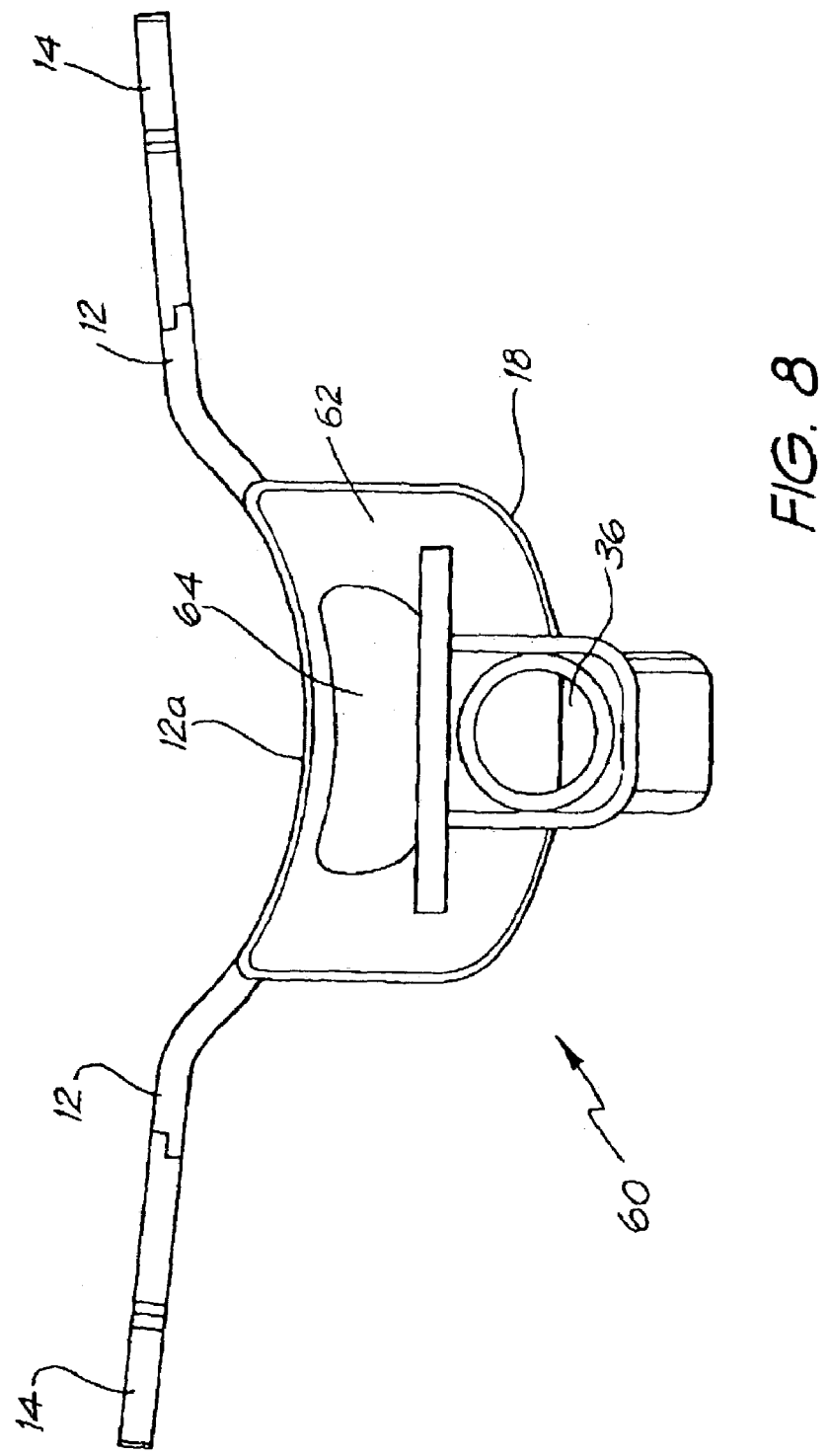
FIG. 8 is a top view of the mask of FIG. 8.
Figure 9:
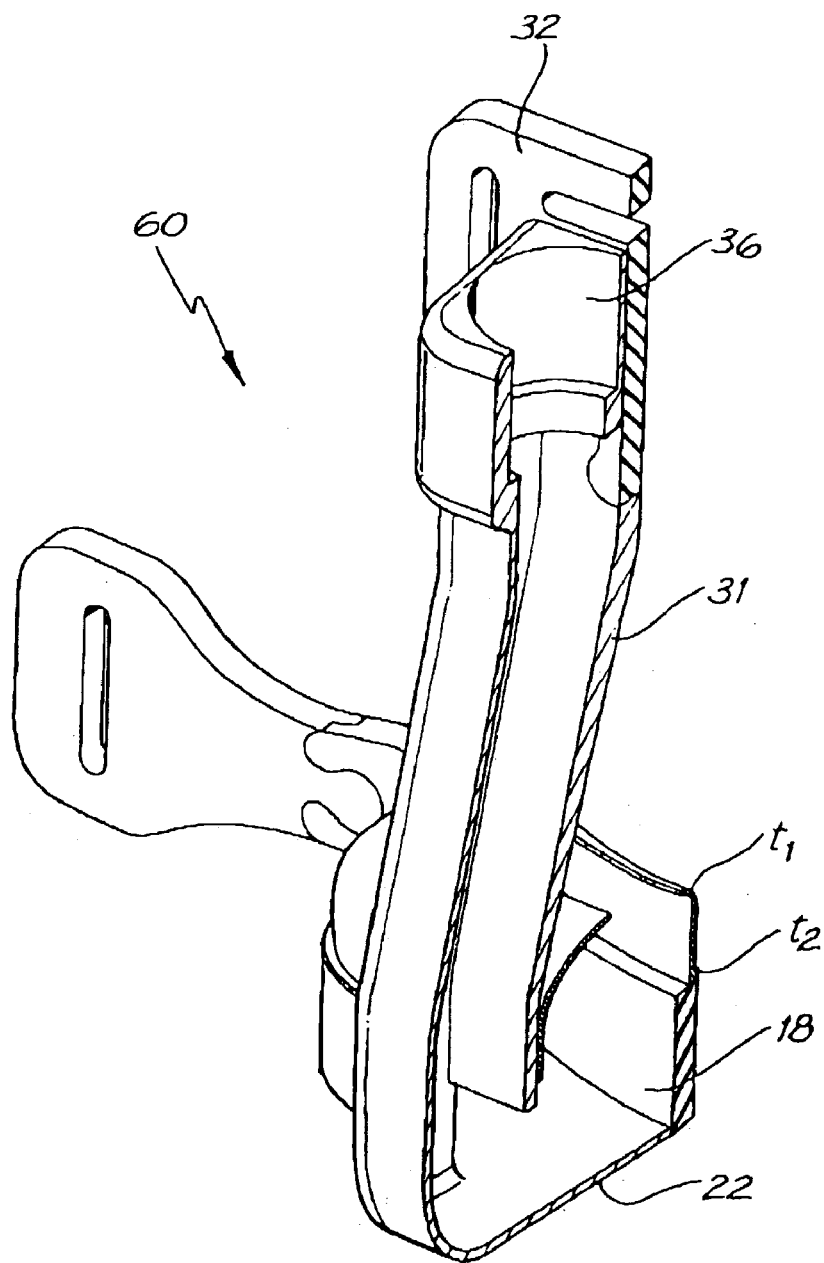
FIG. 9 is a sectional view of the mask of FIG. 8.
Figure 10:
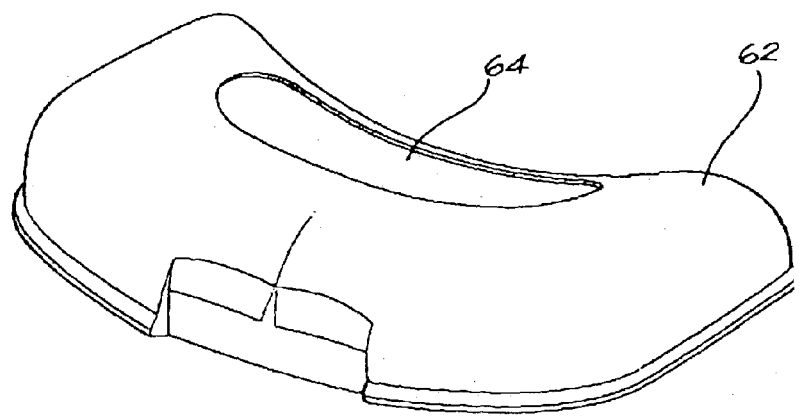
FIG. 10 is an isometric view of a bubble, which forms part of the mask of FIG. 7.

In the second embodiment, the prongs and upper surface of the manifold are replaced with a flexible shaped "bubble" 62, also shown in FIG. 8. The bubble may be made from a flexible elastomeric material (such as silastic). A generally kidney bean shaped opening 64 is provided in the centre of the bubble (see FIG. 9). The bubble ranges in thickness from $t_1$, about 0.2–0.4 mm at the edge around the opening 64 to $t_2$ about 1.5 mm at its base where it joins the manifold (see FIG. 9).

Figure 11A:
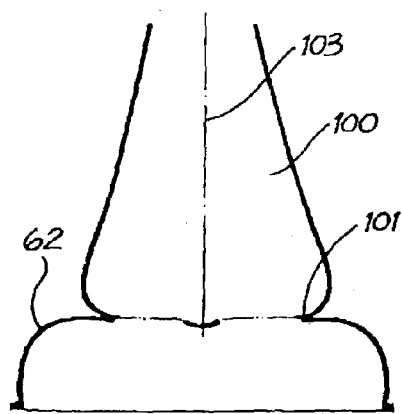
FIGS. 11a and 11b schematically illustrate the bubble and a nose in unexpanded and expanded states respectively.
Figure 11B:
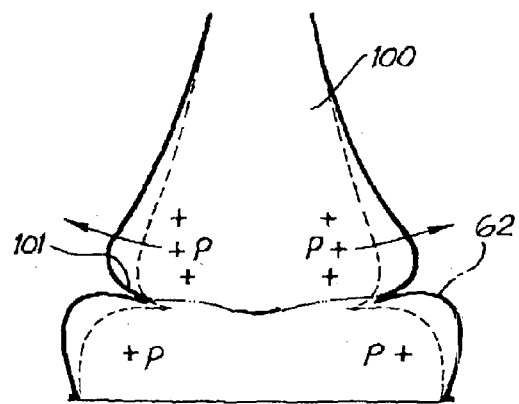
Figure 12:
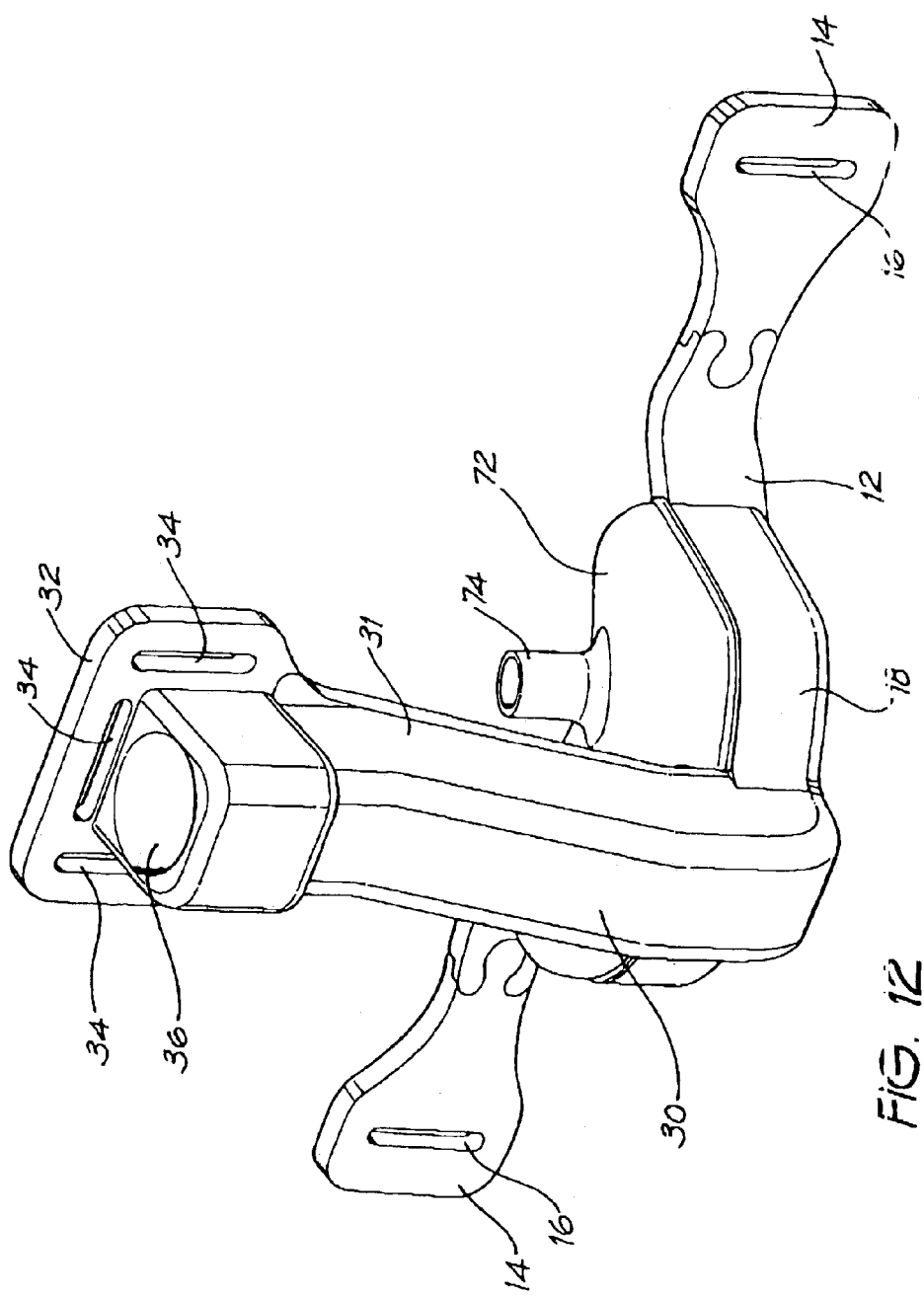
FIG. 12 is an isometric view of a third embodiment of the present invention.

With reference to FIGS. 11a and 11b, in use, when the mask is correctly positioned on a patient's face with the manifold disposed between the base 101 of the patient's nose and their mouth, the membrane 62 is located below the base 101 of the nose. The relatively thin "bubble" is flexible and when air is admitted under pressure into the manifold the bubble expands and will seal three-dimensionally with the base portion 101 of the patient's nose. FIG. 11b illustrates the unexpanded, non-pressurised shape of the bubble in dashed lines and the pressurised form in complete lines illustrating though slightly exaggerating the expansion of the patient's nose. Air under pressure will flow into the patient's nose through their nares. The patient's nose, in particular their anterior nasal cavities, will also expand (see FIG. 11b) and be pushed outwards. This creates a rolling seal at the nasal (naris) entry margins The seal is formed by the skin around the nostrils (under pressure) pushing against the bubble 62 also under pressure. Because both surfaces are under pressure and pushing against each other, a good seal is formed. The improved seal occurs partly because the exterior of the nose is not within the mask and consequently is not pressurised. Since no prongs are located inside a patient's nostrils, the resistance to flow is reduced compared to the first embodiment Further, and equally significantly as the nostrils expand, resistance to air flow also decreases as the surface area of the nostrils opening has increased.

Figure 13:
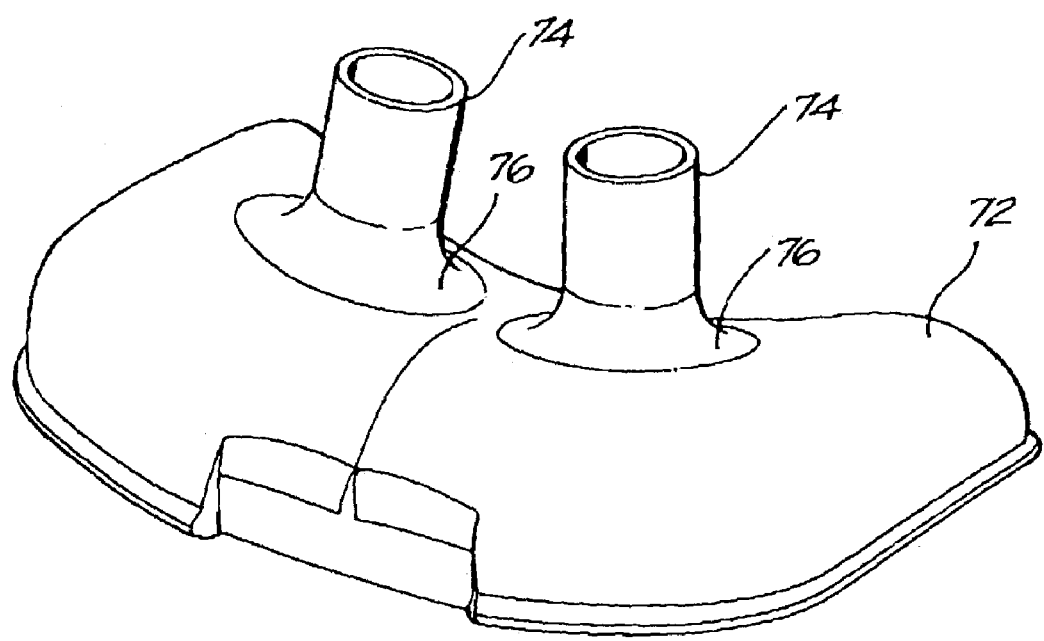
FIG. 13 is an isometric view of a component of the mask of FIG. 12.
Figure 13A:
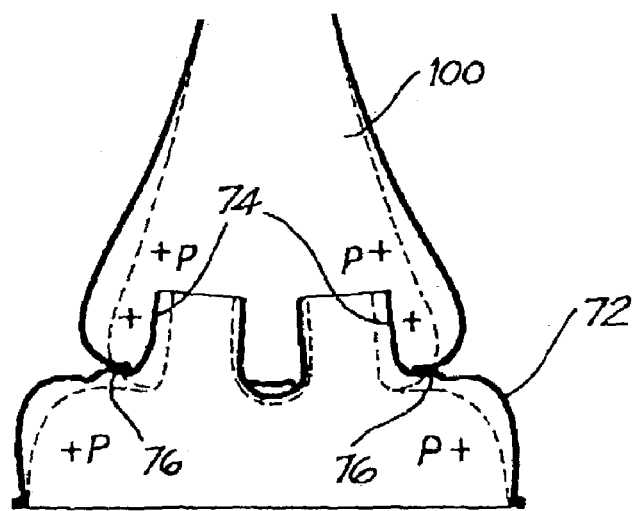
FIG. 13a is a schematic drawing illustrating the expansion of a bubble and nasal prongs of the mask of FIG. 12 in use under pressure in a patient's nose.

FIG. 13 displays a yet further embodiment of the present invention in which instead of the membrane 62, a combined membrane 72 and nasal prongs 74 are provided. The nasal prongs 74 have a thickness of about 0.2–0.4 mm, the same thickness as the upper surface of the membrane 72. The nasal prongs 74 and the part of the bubble membrane 72 around the base of the nasal prongs expand under pressure outwardly, to provide a good seal in the patient's nostrils as is illustrated schematically in FIG. 13a. Again the unexpanded nose and membrane/prongs are shown in dashed lines with the expanded nose and prongs shown in complete lines. The prongs not only expand within the patient's nostrils, but the base 76 of the prongs also expands and seals against the base of the nose around the edges of the patient's nostrils.

Figure 14:
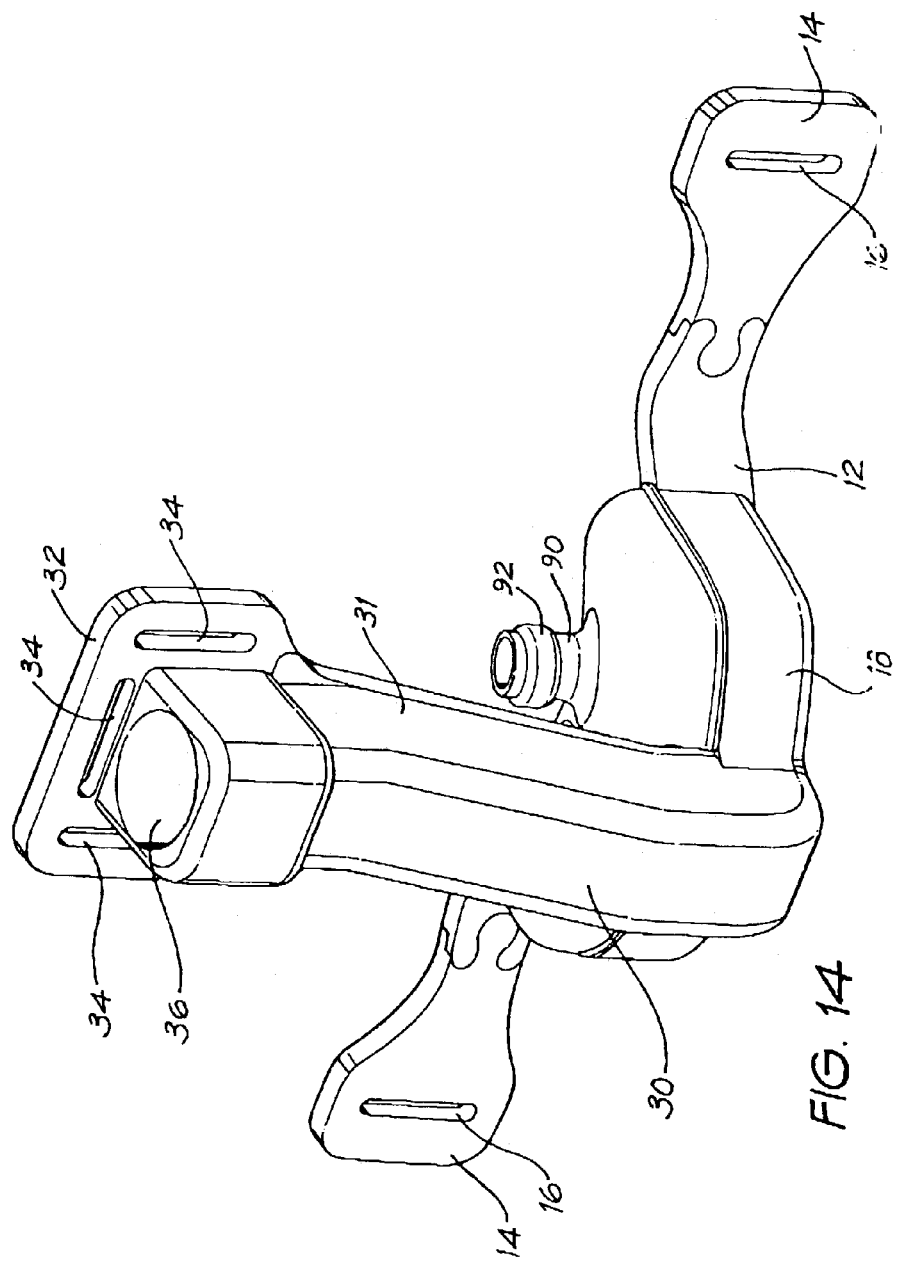
FIG. 14 is an isometric view of a fourth embodiment of the present invention.

FIG. 14 illustrates a yet further variant in which the prongs 90 associated with the bubble are of the type shown in FIG. 4 and include an expanded bubble portion 92 which in use expands and seals within a patient's nostril. Thus the mask seals at the base of the nostril as in the embodiment of FIG. 13 and within the nostril thus providing a double seal.

Figure 15:
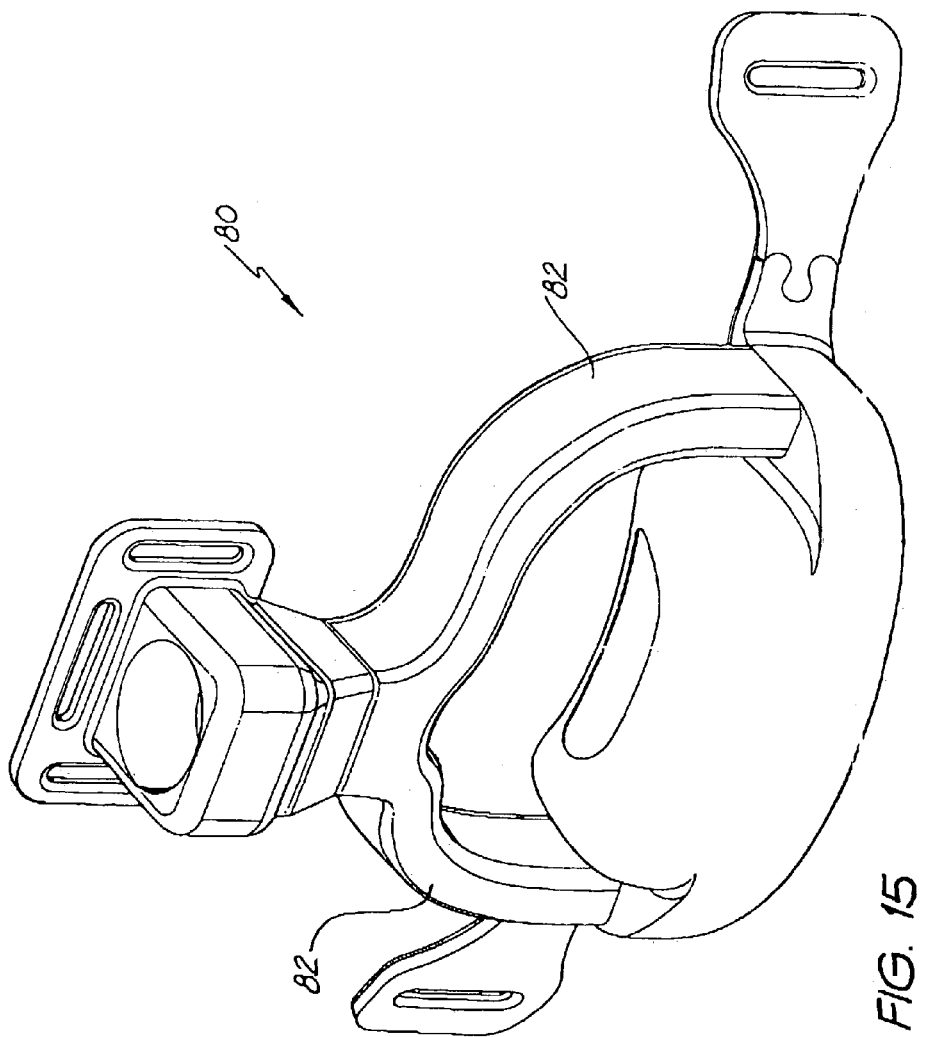
FIG. 15 is an isometric view of a fifth embodiment of the present invention.
Figure 19:
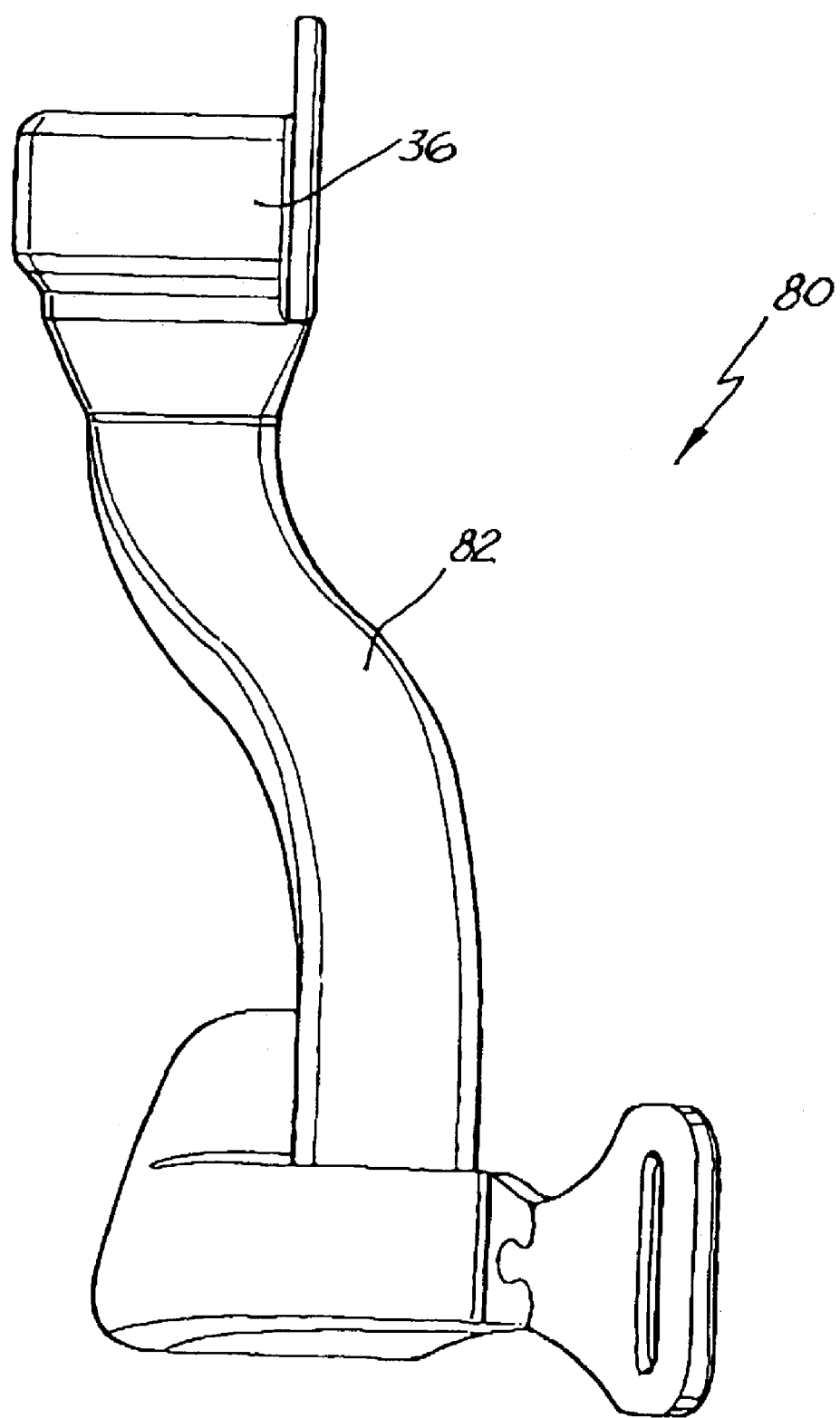
FIG. 19 is a top plan view of the mask of FIG. 15.

FIG. 15 shows a yet further embodiment of the invention in which instead of the bridging portion 31 extending over a patients nose, in the mask 80 of FIG. 15 two pipes or ducts 82 extend from the manifold 18 to the port 36 around the sides of a patient's nose. In use (see FIG. 20) the pipes extend either side of the patient's nose, so that they do not pressurise the patient's nose. This design minimises the foot print of the mask on the patient's face and increases patient comfort. The pipes are curved outwardly to avoid a patient's nose so that the pipes do not prevent the patient's nose from expanding under pressure and do not compromise the seal at the bubble membrane 62 to the base of the patient's nose. The pipes are also angled away from the patient's eye, to allow the patient to see clearly while the mask is on and to allow the patient to read to sleep. As is best seen in FIG. 19 the two pipes are shaped to closely fit to the contours of the patient's face and may also be made relatively flexible to enable this. In this way the pipes function as a barrier between the seal around the patient's nose and the patient's eyes and block/deflect any gas or air leaks escaping from the seal away from the patient's eyes which are sensitive to air leaks.

Figure 16:
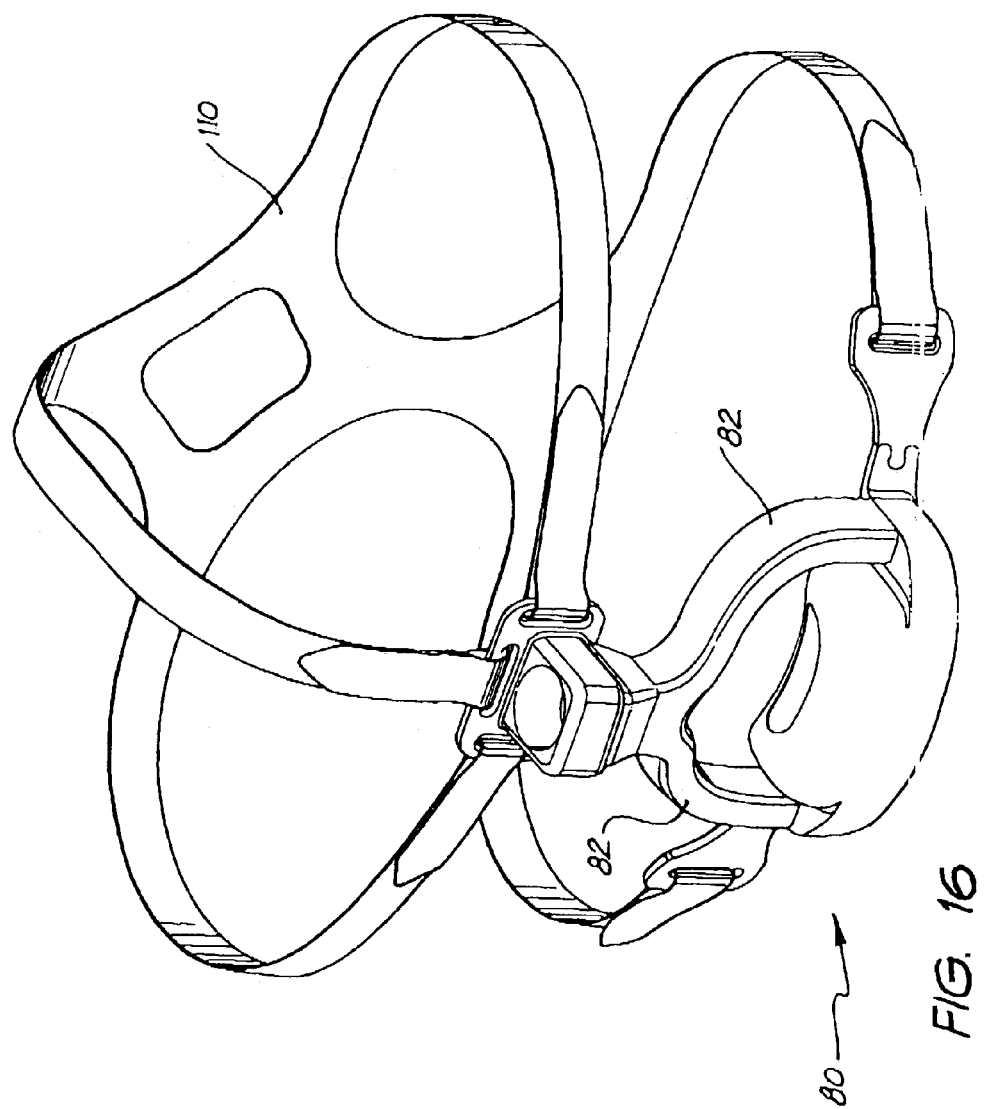
FIG. 16 shows the embodiment of FIG. 15 including a harness.

FIG. 16 shows the mask fixed to a harness 110 for use by a patient.

Figure 17:
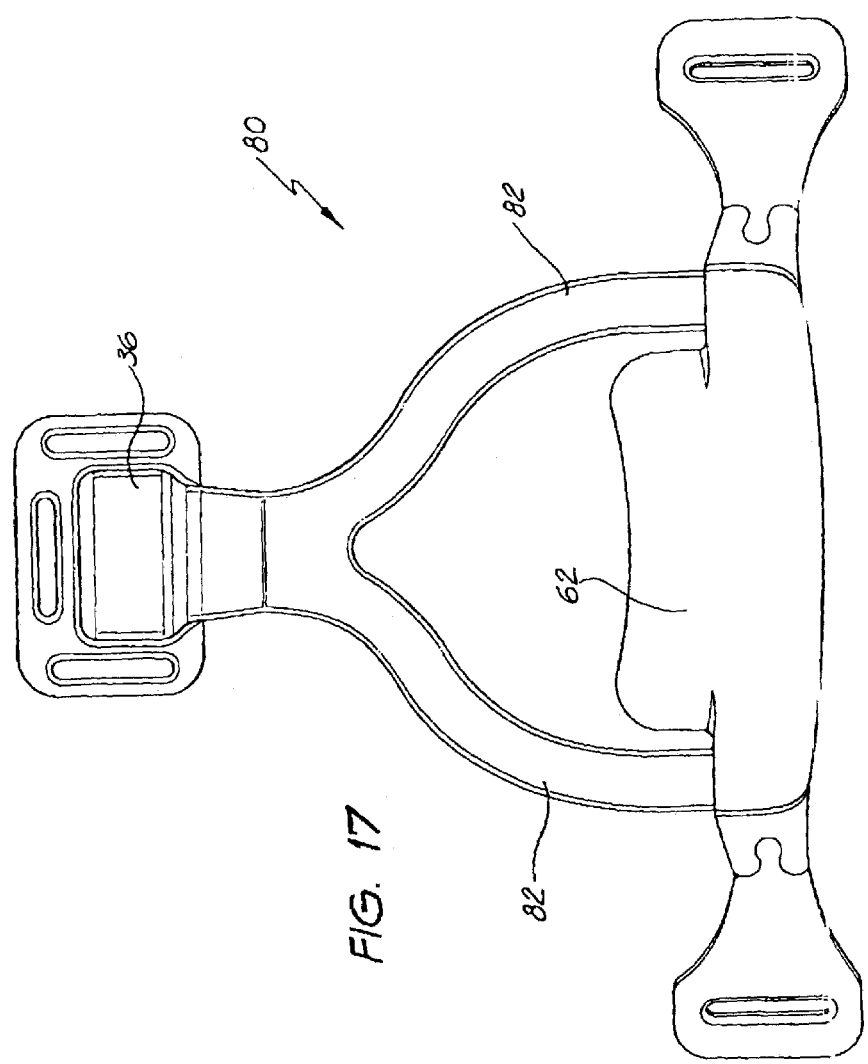
FIG. 17 is a front view of the mask of FIG. 15.

A further feature of the invention which is illustrated in FIG. 17 in particular shows that the pipes 82 extend away from the manifold either side of, and spaced apart from the bubble membrane 62. This feature assists in separating the anchoring function (to which the pipes 82 may contribute from the sealing function provided by the bubble 62.

Figure 18:
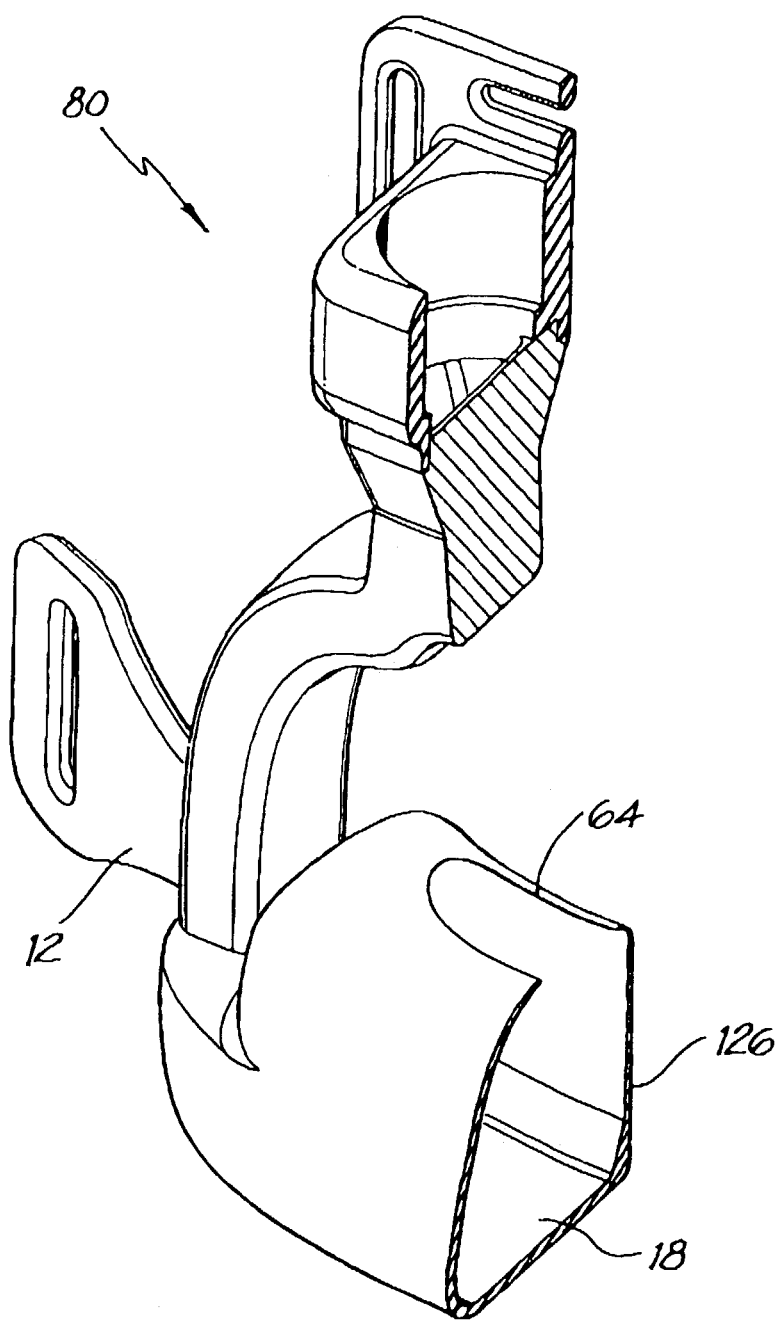
FIG. 18 is a sectional view of the mask of FIG. 15.

FIG. 18 illustrates that the rear wall 126 of the manifold is considerably thinner than the strap 12, typically of the order of 0.2 to 0.4 mm. This improves the sealing of the bubble 64 to the patient's face.

Figure 20:
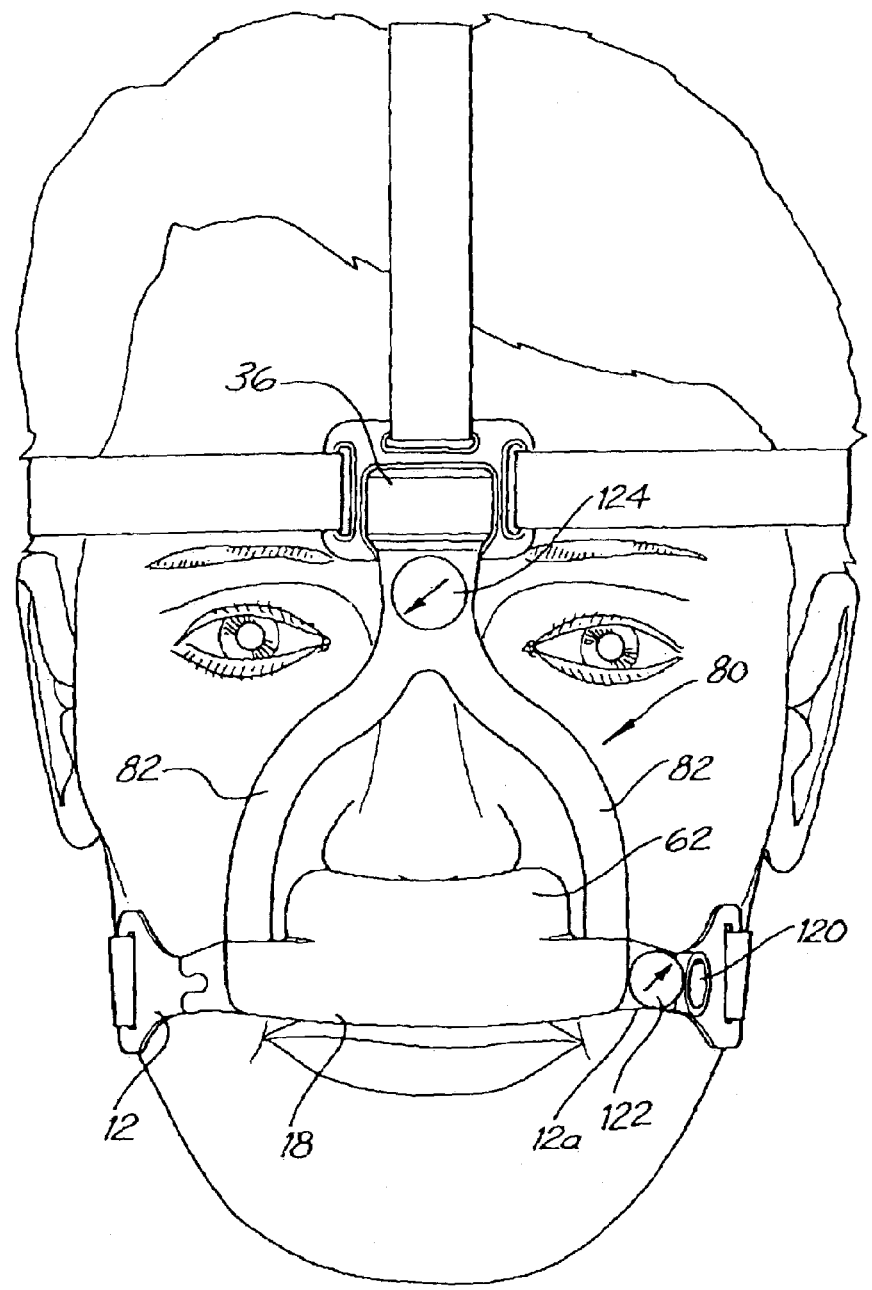
FIG. 20 is a schematic drawing illustrating the use of the mask and harness of FIG. 16.

FIG. 20 also illustrates a further modification of the invention in which air inflow and air outflow is monitored. One of the straps 12 defines a pipe which may be attached to the strap or may have one side wall defined by the strap. Air may flow in through port 36 and flow out via a port 120 at the end of strap/pipe 12*a*. One or more one way valves, not illustrated, would be provided to control the air flow. A meter 122 could be used to measure either the rate of airflow or concentrations of gases such as oxygen or carbon dioxide in the outflow. A similar metering means 124 could be provided in the gas inflow, if desired. Such a mask could be useful in treating stroke victims and the like where a controlled supply of pressurised air or oxygen has to be supplied to the patient since the mask has a low profile it would be more comfortable for the patient than existing CPAP masks.

Figure 21:
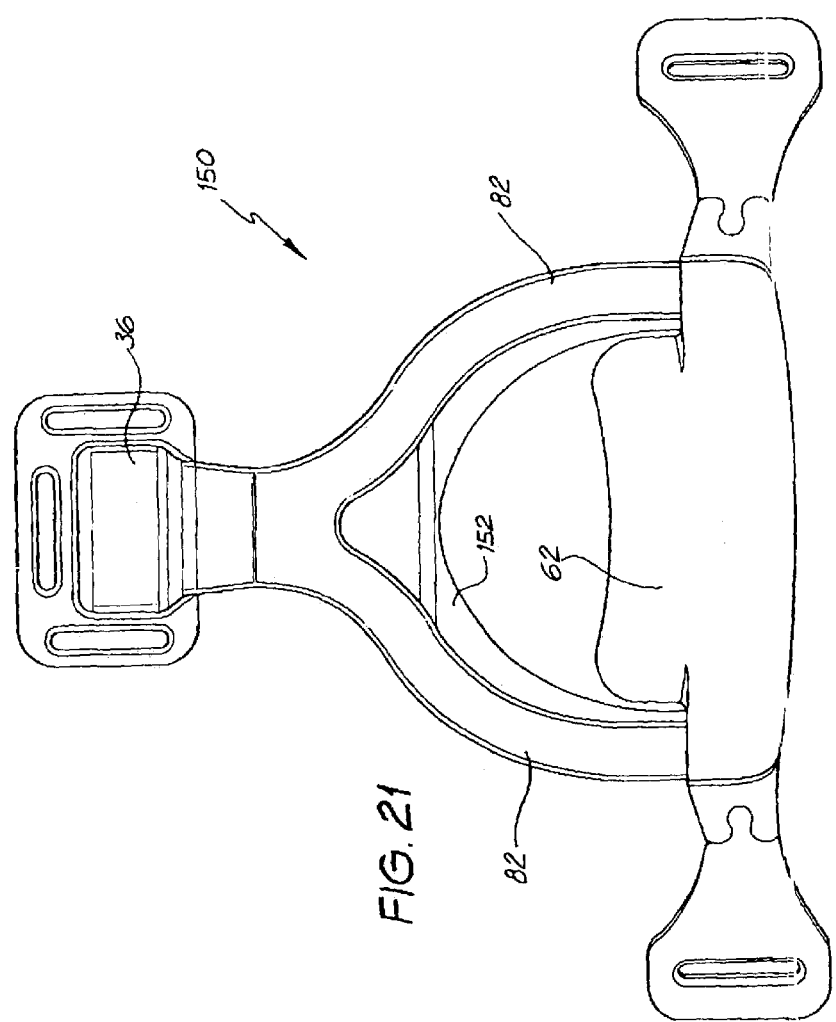
FIG. 21 is a front view of a variant of the mask of FIG. 15.
Figure 22:
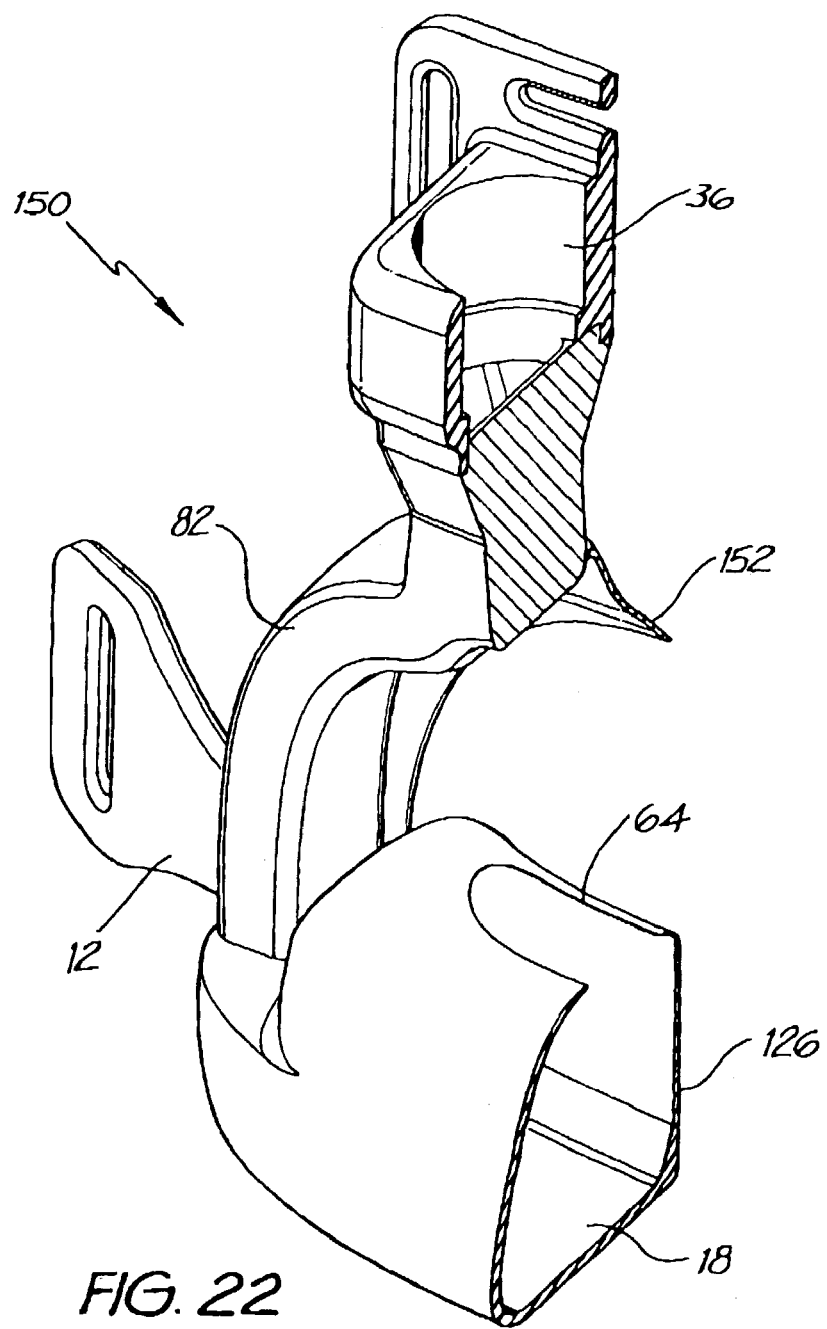
FIG. 22 is a section through the mask of FIG. 21.

Finally FIGS. 21 and 22 illustrate yet further variants of the mask of FIG. 15. The mask 150 is identical to the mask 80 except that a flexible seal 152 in the form of a flap or skirt is defined on the rear of the pipes 82. In use when the mask is located on a patient's face the seal/skirt ensures that any gap between the pipes 82 and the patient's face is closed preventing air leaks from reaching the patient's eyes.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A mask for supplying gas under pressure to the nasal airway of a human comprising:
   a flexible manifold formed from an elastomeric material having a rear wall and including means for connection to a gas supply means;
   a gas delivery element or elements for providing gas under pressure to the nasal air way of a human without pressurising the sides of the nose;
   a flexible strap formed from the same elastomeric material as the manifold for securing the manifold in position on the face of a human, the strap defining a first side, the strap defining and being continuous with the rear wall of the manifold and extending either side of the manifold, the first side of the strap being shaped and configured to generally conform with the shape of the upper lip and adjacent cheek area of a human to act as a distributed anchor for anchoring the mask when the mask is located on said human face, in use, wherein the manifold is disposed to the second side of the strap such that, in use, the manifold is anchored by the strap and by the rear wall but is not compressed between the strap and the human's face.

2. The mask as claimed in claim 1 wherein the gas delivery elements comprise nasal prongs for locating the gas delivery elements inside a human's nostrils.

3. The mask as claimed in claim 1 wherein a nose bridging portion extends from the manifold and is shaped to span the human's nose in use and wherein a distal end of the bridging portion defines a pad which may include a slot for attachment to a harness and an inlet adapted for coupling the nasal mask with a source of gas, the bridging portion being configured, so that in use, when the mask is secured to a human's face, the bridging portion passes over the human's nose.

4. A mask for supplying gas under pressure to the nasal airway of a human, comprising:
   a flexible manifold formed from an elastomeric material having a rear wall and including means for connection to a gas supply means, and a pair of spaced apart gas outlets;
   a pair of gas delivery elements insertable into a human's naris defining a gas flow passageway therethrough coupled with a corresponding gas outlet for conveying gas from the manifold through and out the passageway, the elements being configured to present a distal end portion for insertion into a naris of a human;
   a flexible strap formed from an elastomeric material for securing the manifold in position on the face of the human, the strap being continuous with the rear wall of the manifold and extending either side of the manifold and being shaped and configured to generally conform to the shape of the upper lip and adjacent cheek area of the human to act as a distributed anchor means for anchoring the nasal mask to a human's face.

5. The mask as claimed in claim 4 wherein the strap and manifold are made from the same flexible elastomeric material.

6. The mask as claimed in claim 5 wherein a nose bridging portion extends from the manifold and is configured to pass around or over a human's nose in use to define a further anchoring point distal from the manifold.

7. The mask as claimed in claim 6 wherein two nose bridging portions extend from opposite sides of the manifold and are joined distal from the manifold to define a further anchoring point.

8. A mask for supplying gas under pressure to the nasal airway of a human comprising:
   a manifold including means for connection to a gas supply means and defining a flexible shaped bubble made from an elastomeric material having an aperture therein which is adapted to seal 3-dimensionally to the base of a human's nose supplying air to the human's naris without pressurising the exterior of the human's nose; and
   a flexible strap formed from a flexible elastomeric material for securing the manifold to the face of a human, the strap defining a first side and a second opposite side and extending either side of the manifold, the first side of the strap being shaped and configured to generally conform to the shape of the upper lip and adjacent cheek area to act as a distributed anchor means for anchoring the nasal mask to a human's face when the mask is located on said human face, in use, wherein the manifold is disposed to the second side of the strap such that in use the manifold is anchored by the strap but not compressed between the strap and the human's face.

9. The mask as claimed in claim 8 wherein a nose bridging portion extends from the manifold and is configured to pass around or over a human's nose in use to define a further anchoring point distal from the manifold.

10. The mask as claimed in claim 8 wherein two nose bridging portions extend from opposite sides of the manifold, each nose bridging portion passing between one side of a human's nose and their contiguous eye in use, and wherein the two nose bridging portions together are distal from the manifold to define a further anchoring point.

11. The mask as claimed in claim 10 wherein the two nose bridging portions define a flexible flap which is generally conformable to the shape of a human face to lie against the same, in use.

12. The mask as claimed in claim 8 wherein a pipe extends along at least one side of the strap.

13. The mask as claimed in claim 8 wherein the aperture is of about the size of the base of a human nose.

* * * * *